United States Patent [19]

Cezana

[11] Patent Number: 5,171,245
[45] Date of Patent: Dec. 15, 1992

[54] SURGICAL APPARATUS INCLUDING A SPRING ACTIVATED LOCKING DEVICE

[75] Inventor: Haim Cezana, South San Francisco, Calif.

[73] Assignee: Stryker Corporation, Kalamazoo, Mich.

[21] Appl. No.: 589,418

[22] Filed: Sep. 27, 1990

[51] Int. Cl.⁵ ............................................. A61B 17/00
[52] U.S. Cl. ........................................ 606/86; 606/53; 606/79
[58] Field of Search ..................... 606/53, 79, 80, 86, 606/87, 88, 89, 96

[56] References Cited

U.S. PATENT DOCUMENTS

| | | | |
|---|---|---|---|
| 4,586,496 | 5/1986 | Keller | 606/79 X |
| 4,589,414 | 5/1986 | Yoshda et al. | 606/79 X |
| 4,697,586 | 10/1987 | Gazale | 606/53 |
| 4,798,213 | 1/1989 | Doppelt | 606/80 X |

OTHER PUBLICATIONS

FIGS. 1 and 2, partially broken and central cross-sectional view (1 sheet).
FIGS. 3 and 4, side elevational and central cross-sectional view (1 sheet).
Sketch 1, pictorial view of a tool (1 sheet).
Sketches 2 and 3, aligned and non-aligned flange (1 sheet).

Primary Examiner—Robert A. Hafer
Assistant Examiner—Sam Rimell
Attorney, Agent, or Firm—Flynn, Thiel, Boutell & Tanis

[57] ABSTRACT

Surgical apparatus in which a locking device is provided for releasably securing a surgical tool in a sleeve. A lock housing is movable on the sleeve, the lock housing having a through opening through which the tool is insertable to be received into the sleeve. A lock member on said lock housing has a push button actuable for opening the lock housing to reception of the tool through the through opening and into the sleeve. The lock member has means for automatically locking the tool against removal from said lock housing upon release of the push button. A tapered part on the sleeve receives a correspondingly tapered portion of the tool to thereby assure a snug fitting connection of said sleeve with the tool. A hand engageable portion on the lock housing is actuable for pulling the lock housing axially with respect to said sleeve in a direction opposite the direction in which the tool is inserted into the sleeve and for engaging the lock member with a corresponding part of the tool and thereby for positively axially holding together the tapered parts of the sleeve and tool while locking the tool axially with respect to the sleeve.

14 Claims, 3 Drawing Sheets

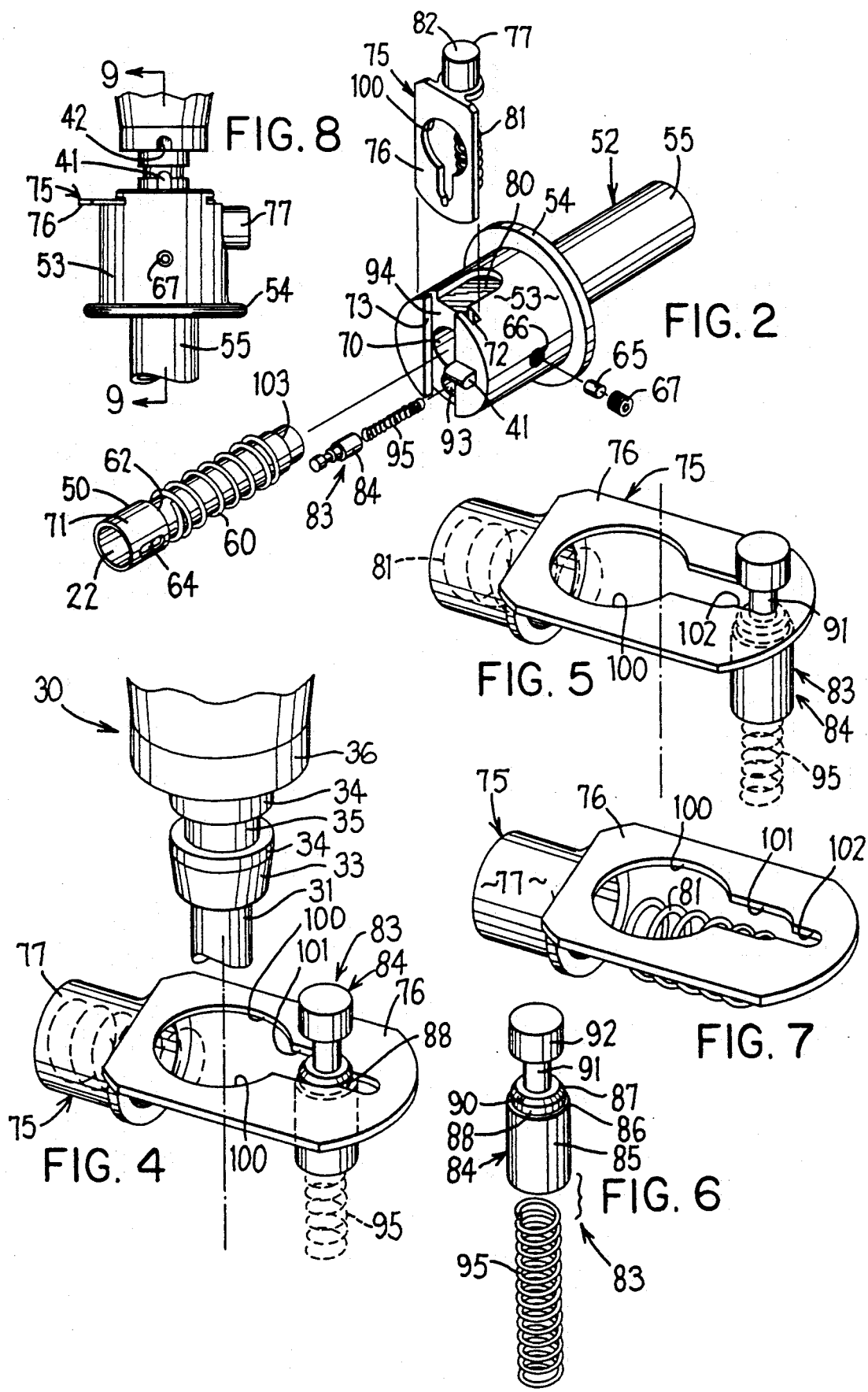

SURGICAL APPARATUS INCLUDING A SPRING ACTIVATED LOCKING DEVICE

FIELD OF THE INVENTION

This invention relates to a surgical apparatus including a locking device for axially releasably locating an inner surgical tool within an outer sleeve.

BACKGROUND OF THE INVENTION

It has been known in arthroscopic surgical procedures, to enter a surgical site, for example a knee joint, with an elongate entry tool, such as a trocar, sheathed in a snug fitting outer sleeve. Thereafter the entry tool is removed, leaving the entry end of the sleeve at the surgical site and the other end of the sleeve protruding from the patient. Thereafter, one or more additional elongate surgical tools, such as an arthroscope or obturator can, in desired sequence, be alternately inserted through the sleeve to reach the surgical site.

Further, it is known to equip the sleeve for connection to an irrigation liquid source for injecting irrigation liquid therethrough into the surgical site, and for connection to a suction source for removing flowable material from the surgical site.

In each instance, the sleeve, extending into the surgical site, acts as a conduit of access to the surgical site from outside the body of the patient and permits a variety of surgical procedures to be performed without requiring more than the very small incision needed to insert the sleeve.

In prior devices of this type, the outer end of the sleeve is provided with a manually actuable locking device engageable with a connector on the tool for at least axially fixing the tool within the sleeve. However, prior locking devices of which I am aware have not been entirely satisfactory.

In one such prior locking device, a threaded member must be rotated with respect to the sleeve to lock and unlock a tool with respect to the sleeve. However, some surgeons have confused the lock and unlock rotation directions. Further, the threaded member may become slippery during surgery and require extra care to lock and unlock. Further, a surgeon may fail to fully rotate the threaded member and thus need to repeat the rotation.

Accordingly, the objects and purposes of this invention include provision of a locking device for axially releasably locating an inner surgical tool within an outer sleeve, in which it is intended to improve upon prior locking devices, in which locking and unlocking of the tool with respect to the sleeve can be done with one hand, in which locking and unlocking require distinctively different kinds of manipulation and can readily be done without significant training by surgical personnel and despite the presence of liquids or slippery materials on the tool and sleeve, in which the locking is positive and will retain a tool in the sleeve despite feeding of liquid under pressure into a space between the sleeve and tool and toward the wound and despite possible liquid pressure tending to push the tool outwardly out of the sleeve.

Further objects and purposes of the invention will be apparent to persons acquainted with apparatus of this general type upon reading the following specification and inspecting the accompanying drawings.

SUMMARY OF THE INVENTION

A surgical apparatus, in which a locking device releasably secures a surgical tool in a sleeve, comprises a tool receiving sleeve and a lock housing on the sleeve. The lock housing head has an opening through which the tool is insertable into the sleeve. A lock member is actuable for opening the lock housing to release a previously loaded tool or receive a tool. The lock housing is actuable for locking received tool in the sleeve.

BRIEF DESCRIPTION OF THE DRAWINGS

FIG. 2 is an enlarged, exploded view of the tool lock device of the apparatus of FIG. 1.

FIG. 4 is an enlarged fragmentary exploded view of a portion of a tool as it approaches the open lock plate of the tool lock device prior to locking.

FIG. 5 is an enlarged exploded view similar to FIG. 4 but with the lock plate in its closed position for locking together the tool and sleeve in their FIG. 1 use position.

FIG. 6 is an enlarged exploded view of the release pin and its spring of FIGS. 4 and 5.

FIG. 7 is an enlarged exploded view of the lock plate unit of FIGS. 4 and 5.

FIG. 8 is a fragmentary elevational view of the locking device of FIG. 1 and substantially taken on the line 8—8 of FIG. 1.

DETAILED DESCRIPTION

Figure 1:
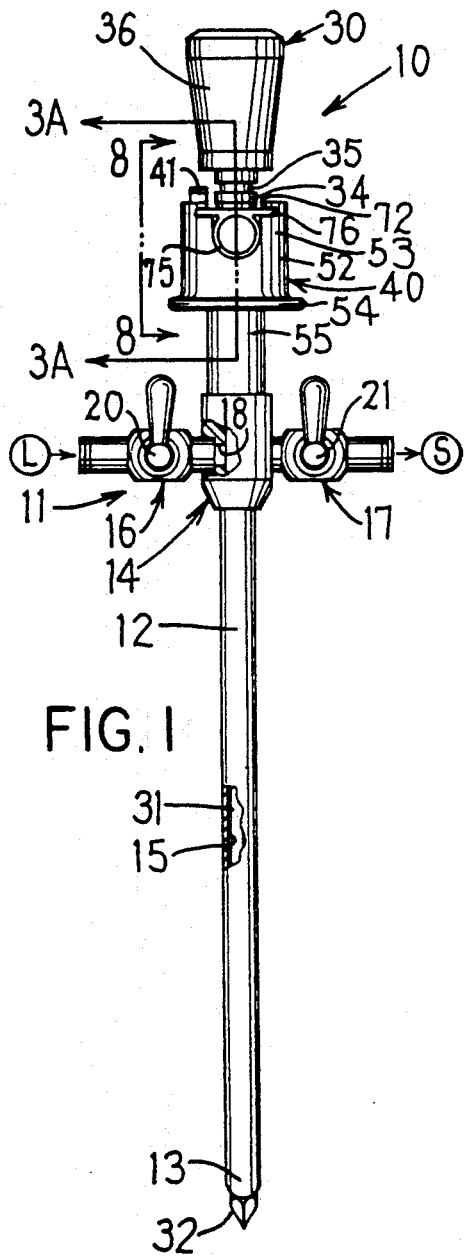
FIG. 1 is an elevational view of a surgical apparatus embodying the invention.

A surgical apparatus 10 (FIG. 1), particularly usable in arthroscopic surgery, comprises a hollow, elongate sleeve 11 having a central passage 15. The sleeve 11 includes an elongate hollow sleeve element 12 having a lower end 13 insertable into the tissue of a patient, namely into an inspection or surgical site (not shown) therein.

The sleeve 11 further includes a fitting 14 (FIG. 3C) fixed, as by press fit, over the top of the sleeve element 12. The fitting 14 is hollow and continues the central passage 15 through the sleeve. Stopcocks 16 and 17 (FIG. 1) extend radially and fixedly from the fitting 14, on opposite sides thereof, and are connectable to sources L and S respectively of irrigant liquid and suction, or to other suitable fluid connections. The stopcocks communicate, as generally indicated at 18 (FIGS. 1 and 3C) with the central passage 15 of the sleeve 11. The stopcocks are equipped with valves 20 and 21 manually actuable to open and close communication between the central passage 15 and sources L and S, respectively, and thereby with the surgical site into which the lower end 13 of the sleeve 11 extends during surgery. The central passage 15 continues upward coaxially through the sleeve 11 and its upper end portion widens upwardly to form a widened frustoconical mouth 22 to facilitate downward reception of a tool therethrough.

Figure 3A:
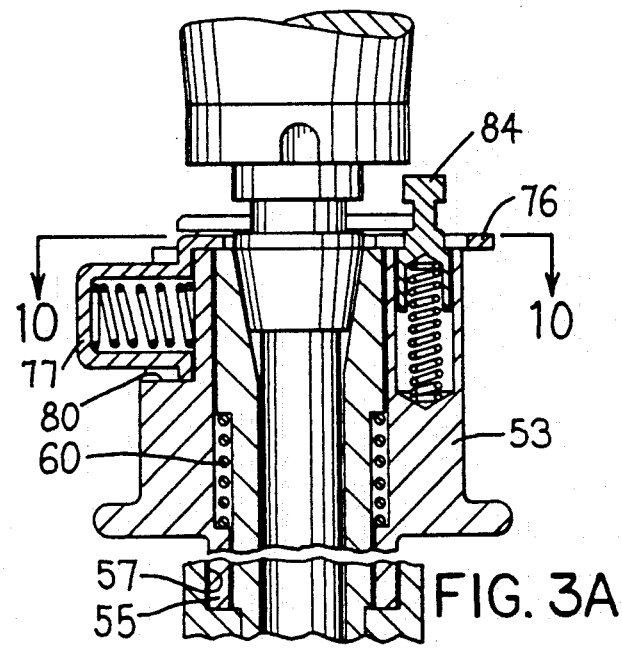
FIGS. 3A, 3B and 3C are enlarged fragmentary central cross sectional views each taken on the line 3—3 of FIG. 1 and showing a sequence of positions of parts taken during installation of a tool in the sleeve and tool lock device from which the sleeve extends.
Figure 3B:
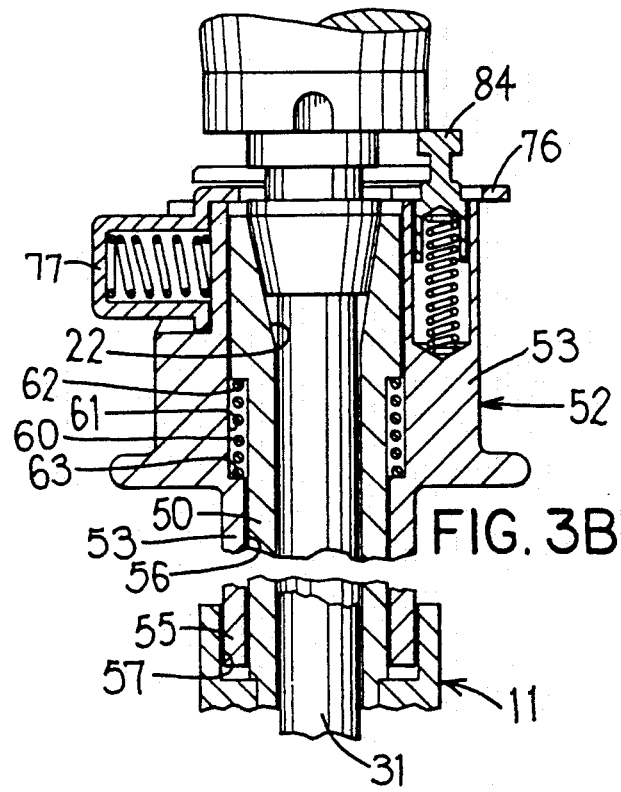
Figure 3C:
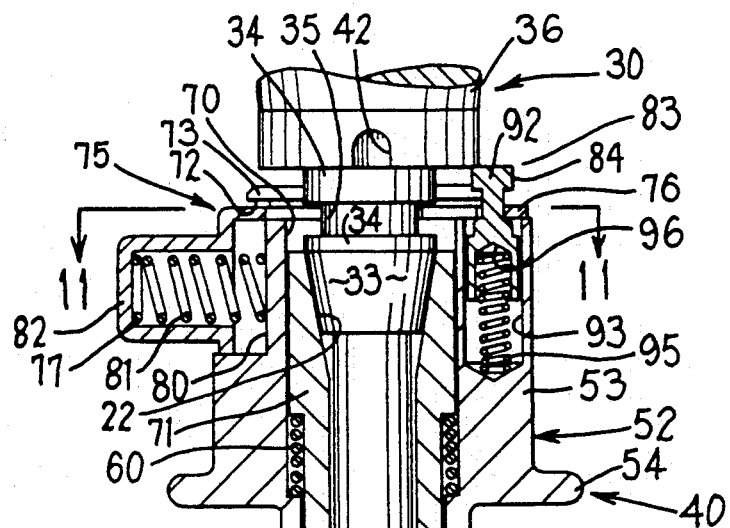

The sleeve 11 is intended to alternatively receive a variety of tools during the course of a surgical procedure. Examples of tools include a trocar, an arthroscope or an obturator, among others. By way of example, the tool 30 shown in FIGS. 1 and 3C is a trocar.

Each tool 30 has an elongate shank 31 which is installed by inserting its patient engaging, bottom end 32 (FIG. 1) downward into the upward opening, frustoconical mouth 22 of the sleeve 11 and then allowing the tool shank 31 to slide downwardly through the central passage 15 until its patient engaging bottom end 32 reaches substantially the lower end 13 of the sleeve 11 (in the embodiment shown, protruding down and slightly therebeyond). The shank 31 fits within the central passage 15 of the shell 11 closely, but with enough clearance to permit fluid flow in the annular space between the shank 31 and the peripheral wall of the central passage 15. Such flow is axially between the stopcocks 16 and 17 and the lower end 13 of the sleeve 11, for example, to permit irrigant liquid from the source L to travel down the outside of the shank 31 to the surgical site or to allow suction by the source S of flowable materials from the wound site toward the suction source S. In the embodiment shown, the passage 15 and shank 31 are both substantially cylindrical.

Integral with the upper end portion of the shank 31, the tool 30 includes a downward tapering, frustoconical portion 33 (FIG. 3C) for seating snugly and sealingly in the frustoconical mouth 22 when the shank 31 is inserted fully into the sleeve 11.

To lock and unlock the tool 40 with respect to the sleeve 11, a lock device 40 is provided atop the sleeve 11 and interacts between the sleeve 11 and tool 30.

To the extent above described, the surgical apparatus 10 is substantially conventional.

Turning now to aspects of the surgical apparatus 10 more specifically embodying the present invention, the tool 30 includes a cylindrical portion 34 (FIGS. 1 and 3C). Spaced between the ends of the cylindrical portion 34 is an annular lock groove 35. The tool 30 includes a radially enlarged head 36 extending upward integrally and coaxially from the cylindrical portion 34, in spaced relation above the annular lock groove 35. The head 36 is shaped for convenient hand engagement by the user, particularly in inserting the tool 30 into the sleeve 15 and withdrawing same upwardly out of the sleeve.

It may be desired to prevent rotation of the tool 30 with respect to the sleeve 11. To that end, an upstanding, eccentrically located lug 41 (FIG. 1) is engagable with a shallow notch 42 (FIG. 3C) in the bottom peripheral edge of the head 36.

The sleeve 11 includes an upward extension 50 (FIG. 3C) having a lower end portion sealingly fixed by set screws 51 in an upward opening bore 43 in the fitting 14. The extension 50 (or taper housing) thus sealingly continues upward the central passage 15, and indeed, at its upper end, carries the frustoconical mouth 22. In the embodiment shown, it is the interior of the sleeve extension 50 which communicates at 18 with the stopcocks 16 and 17. The snug connection of the sleeve element 12 and sleeve extension 50 in coaxially communicating recesses in the fitting 14 assures a continuous leak-proof liquid or gas communication between the fitting 14 and the lower end 13 of the sleeve element 12.

The snug tapered fit of the installed frustoconical portion 33 of the tool 30 in the frustoconical mouth 22 at the top of the central passage 15 of the sleeve 11 assures that no fluid leakage occurs therebetween, thereby preventing drawing of air downward through the frustoconical mouth 22 into the central passage 15 and further assuring no escape of liquid upward out of the central passage 15 past the frustoconical mouth 22, when the tool 30 is fully installed in and locked into the upper end of the sleeve 11.

The lock device 40 in the preferred embodiment of the invention includes a lock housing 52 (FIGS. 1 and 3C). The lock housing 52 has upper, mid and lower parts respectively defining a substantially cylindrical body 53, a radial flange 54 and a depending tubular skirt 55. The lock housing 52 has a central bore 56 in which is received the upward extension 50 of the sleeve 11. The lower end of the skirt 55 is snugly but slidably received coaxially in an upward opening annular recess 57 (FIG. 3C) in the top of the fitting 14. A coil compression spring 60 (FIGS. 3B and 3C) urges the lock housing 52 downward with respect to the sleeve 11, to bottom the skirt 55 in the annular recess 57 as seen in FIG. 3A. The spring 60 is housed in an annular space 61 (FIG. 3B) defined axially between a downward facing radial step 62 in the upward extension 50 of the sleeve 11 and an upward facing radial step 63 in the central bore 56 of the lock housing 52. The annular space 61 is located axially near the bottom of the body 53 and below the frustoconical mouth 22. The opposing steps 62 and 63 have a radial width somewhat exceeding the radial extent of the spring 60 so that the spring 60 clears the proposed inner and outer cylindrical surfaces of the body 53 and sleeve extension 50 sufficient to enable free telescoping movement of the lock housing 52 on the sleeve extension 50. The spring 60 resiliently bottoms the lower end of the skirt 55 in the annular recess 57 to prevent the lock housing 52 from escaping upwardly off the top of the sleeve 11, and for determining the lowermost position of the lock housing 52, on the upward sleeve extension 50, as shown in FIG. 3A.

Figure 9:
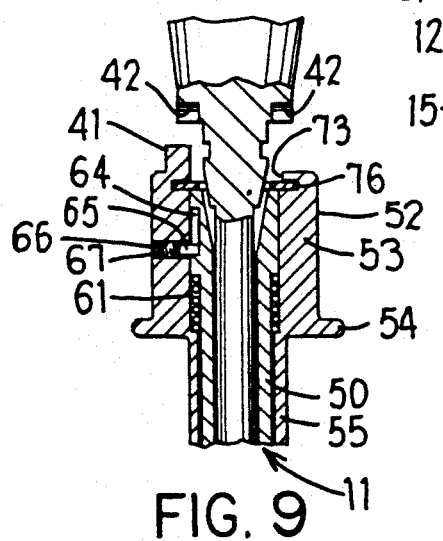
FIG. 9 is a sectional view substantially taken on the line 9—9 of FIG. 8.

Relative rotation between the lock housing 15 and sleeve 11 is prevented as indicated in FIG. 9. More particularly, a radially outwardly facing, axially extending, axially blind groove 64 in the sleeve extension 50 is vertically spaced between the spring annular space 61 and the frustoconical mouth 22. An anti-rotate pin 65 (FIGS. 2 and 9) is inserted through a radial hole 66 in the body 53 of the lock housing 52 and enters the groove 64 to prevent relative rotation between the lock housing 52 and sleeve 11. A set screw 67 is threaded into the outside portion of the hole 66 to prevent nonintended escape of the pin 65 from the groove 64. The top and bottom of the groove 64 may be located to provide an additional or alternative set of limits of vertical displacement of the lock housing 52 on the sleeve 11.

In view of the upward facing step 63 (FIG. 3B), the central bore 56 of the lock housing 52 forms a deep, somewhat enlarged diameter, recess 70 into which the somewhat enlarged diameter top portion 71 (FIGS. 2 and 3C) of the sleeve upward extension 50 is snugly but slidably received.

An undercut groove 72 (FIGS. 1, 2 and 9) extends diametrally across the top of the lock housing body 53. The open top 73 of the groove is of lateral width slightly exceeding the diameter of the recess 70. The undercut groove 72 opens at its opposite ends diametrally through the periphery of the lock housing body 53. The length edges 74 of the undercut portion of the undercut groove 72 are spaced laterally apart a distance substantially exceeding the diameter of the recess 70, as can be seen from FIGS. 2, 10 and 11.

A lock member 75 (FIG. 7) comprises a lock plate 76 having a lock cup 77 at one end thereof. The lock plate 76 is snugly but slidably received diametrally in the undercut groove 72 as indicated in FIGS. 1, 2, 3C and 8–11.

Figure 10:
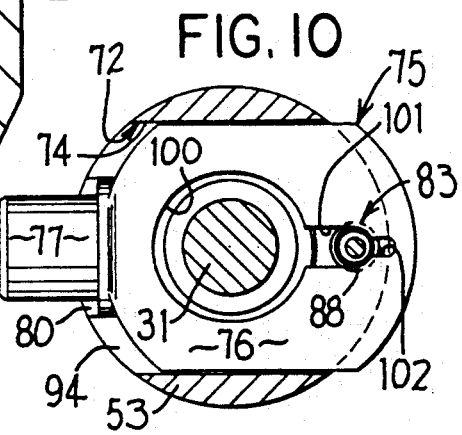
FIGS. 10 and 11 are sectional views substantially taken on the line 10—10 of FIG. 3A and 11—11 of FIG. 3C, respectively.
Figure 11:
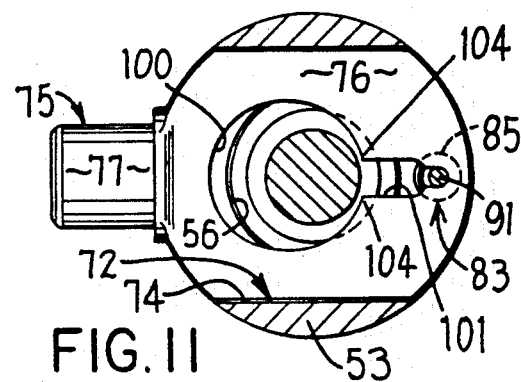

The lock cup 77 depends from one end (the left end in FIG. 3C) of the lock plate 76 in a rigid fashion, extends leftwardly beyond the lock plate 76 and opens rightwardly into the space under the lock plate and along the length direction of the lock plate. With the lock plate 76 extending along the undercut groove as shown in FIGS. 3C, 10 and 11, the cup 77 opens rightwardly toward a radially shallow recess 80 (FIGS. 2, 3C and 10) in the peripheral wall of the lock housing body 53. The recess 80 is generally U-shaped in elevation as seen in FIG. 2 and is sized to laterally receive the lock cup 77 in at least partially recessed relation therein throughout the normal range of lateral movement of the lock plate 76 in the undercut groove 72.

A lock spring 81, here a coil spring of compression type, is compressed diametrally of the lock housing body 53, between the closed leftward end 82 of the lock cup 77 and the opposed upstanding wall of the recess 80, so as to continuously resiliently urge the lock plate 76 leftwardly in FIGS. 3C, 10 and 11, and thereby in the normal direction of withdrawal of the lock plate 76 from the undercut groove 72 during disassembly of the apparatus. The spring 81 is prevented from sliding the lock member 75 leftwardly (FIG. 3C) off the lock housing 52, and indeed the lateral position of the lock plate 76 in the undercut groove 72 is determined, by a release unit 83.

The release unit 83 (FIGS. 3C, 4–6, 10 and 11) comprises a release pin 84 (FIGS. 4–6) comprising a cylindrical base 85 (FIG. 6) which defines the maximum diameter of the pin. Above the cylindrical base 85, the pin 84 has two successive upward facing steps 86 and 87 (FIG. 6) which are separated by medium width part 88 of substantially cylindrical configuration, topped by an upward tapering annular bevel 90. The release pin 84 further comprises a cylindrical narrow width part 91 topped by an enlarged diameter head 92.

The release pin 84 is receivable for its entire length downward into an upward opening blind hole 93 (FIGS. 2 and 3C) in the lock device body 53. The blind hole 93 opens upward through the bottom 94 of the undercut groove 72 adjacent the end thereof furthest from the recess 80. The blind hole 93 is generally centered in the undercut groove 72 and is closely spaced from the recess 70. A coil compression spring 95 is trapped axially between a downward opening recess 96 (FIG. 3C) in the bottom of the release pin 94 and the bottom of the blind hole 93 in the body 53. The spring 95 is sized to continuously urge the release pin 84 upward out of the blind hole 93.

To enable it to coact with the tool 30 and release pin 84, the lock plate 76 has a relatively large diameter hole 100 (FIG. 7) opening therethrough. The hole 100 is laterally centered between the side edges of the lock plate 76 and is nearer to the lock cup 77 than to the opposite end of the lock plate. A notch 101 communicates with the hole 100, is centered between the side edges of the lock plate, and extends from the hole 100 in a direction away from the cup 77. A notch extension 102 (FIG. 7) communicates with and extends beyond the closed end of the notch 101 in a direction away from the cup 75. The notch extension 102 is centered between the side edges of the lock plate 76. The blind end of the notch extension 102 is close to but spaced from the end of the lock plate 76 remote from the cup 77 (the right end in FIG. 7). The lateral widths of the hole 100, notch 101 and notch extension 102 are, respectively, relatively wide, of medium width and of relatively narrow width. The hole 100 is circular and of diameter a bit larger than the diameter of the cylindrical portion 34 of the tool 30 (FIG. 4), so as to allow insertion of the portions 31, 33, 34 and 35 of the tool downward therethrough, in the manner seen, for example, in FIG. 3C. The notch 101 is of lateral width to permit snug but slidable reception therein of the medium width part 88 of the release pin, as shown in FIGS. 3A, 3B, 4 and 10. The notch extension 102 is of width sufficient to snugly but slidably receive the narrow width portion 91 of the release pin 84 as seen, for example, in FIGS. 3C, 5 and 11. The notch extension 102 is too narrow to receive the medium width portion 88 or head 92 of the release pin 84.

OPERATION

The apparatus 10 (FIGS. 2 and 3C) can be assembled as follows. The top of the sleeve element 12 is fixed, as by a press fit or an adhesive or as desired, in the bottom of the fitting 14. The fitting 14 receives the lock housing skirt 55 downward into its annular recess 57 (FIG. 3C). The relaxed spring 60 is dropped into the upfacing recess 70 in the body 53, to rest on the upward facing step 63 (FIG. 3B). The sleeve upward extension 50, with its top portion 71 upward, is then dropped into the recess 70 of body 53 and its step 62 comes to rest upon the top of the spring 60. Set screws 51 affix the sleeve upward extension 50 within the fitting 14. To assure sinking of the skirt 55 to the proper depth in the fitting 14, the skirt 55 preferably has a downward facing step 103 (FIGS. 2 and 3C) which seats upon the bottom of the annular recess 57 in the fitting 14.

The pin 65 and set screw 67 (FIG. 9) are installed in the body 53 with the pin 65 slidably lodged in the groove 64 in the sleeve extension 50, so as to prevent rotation of the sleeve extension 50 within the lock housing body 53.

The release pin spring 95 and release pin 84 are successively dropped into the blind hole 93 (FIG. 3C) in the top of the body 53. The lock plate 76, with the spring 81 captive in the cup 77, is slid (rightwardly in FIG. 3C) into the undercut groove 72 in the body 53. To permit complete insertion of the lock plate 76, the release pin 84 is manually held down with its head 92 below the bottom 94 of the undercut groove 72, thereby allowing the lock plate to slide rightwardly (FIG. 3C) over the top of the release pin 84. Continued rightward sliding of the lock plate 76 brings the notch extension 102 and then the notch 101 over the top of the release pin 84. When the notch 101 is over the top of the release pin, the release pin is allowed to rise into the notch 101 until its lower step 86 hits the bottom of the lock plate 76, as in FIGS. 3A, 3B, 4 and 10. In this position, the release pin 84 prevents leftward (FIG. 3C) escape of the lock member 75 from atop the body 53, and the bottom of the lock plate 76 bears upon the lower step 86 of the release pin 84 to prevent upward escape of the release pin from the body 53.

With the apparatus 40, 11 assembled in the manner above discussed, a tool 30 can be installed therein as follows.

Prior to inserting the tool 30, the lock member 75 is shifted to its open position (with its hole 100 coaxial with the sleeve 11), shown in FIGS. 3A and 10. Then, the bottom end 32 (FIG. 1) of the tool 30 is dropped into the frustoconical mouth 22 of the sleeve central passage 15, until the bottom of the head 36 of the tool 30 comes to rest upon the upward protruding lug 41 (FIGS. 2 and 9). The open lock member 75 permits tool shank 31 and frustoconical portion 33 and the lower cylindrical portion 34 (FIG. 4) to pass downward through the lock plate hole 100. The tool head 36 is then rotated sufficient to bring one of the notches 42 into position above the lug 41 (as in FIG. 8), thereby allowing the tool 30 to drop slightly further into the sleeve central passage 15, indeed until the frustoconical portion 33 of the tool fits sealingly in the frustoconical mouth 22 (FIG. 3C). The annular groove 34 of the tool 30 thus lies in the same radial plane as the lock plate 76. The tool 30 is thus properly vertically located in the sleeve 11 but is not locked therein.

The tool 30 is locked into the lock device 40 and sleeve 11 as follows. With one of the notches 42 receiving the lug 41, the head 36 of the tool 30 can be palmed by the user and the first two fingers of the user's same hand can straddle the skirt 55 and then pull up on the underside of the radial flange 54 of the lock housing 52 to raise the lock housing 52 from its FIG. 3A position to its FIG. 3B position to its FIG. 3C position on the sleeve 11. This compresses the spring 60 and causes the bottom of the tool head 36 to depress the release pin 84 sufficient to drop its medium width portion 88 and bevel 90 below the lock plate 76 (see the transition from FIG. 3B to FIG. 3C and from FIG. 4 to FIG. 5). Thus, the spring 81 is free to displace the lock plate 76 leftward from its FIG. 3B and 10 open position to its FIG. 3C and 11 closed position. This brings the ear-like edges 104 (FIG. 11) of the lock plate 76, where the hole 100 meets the notch 101, into the annular groove 35 in the tool 30, as shown in FIGS. 3C and 11, and thereby prevents the tool 30 from being pulled upward out of the lock housing 52 and sleeve 11.

The lock member 40 is then be released and the spring 60 will push same downward on the sleeve upward extension 50, enough to resiliently urge the lock plate 76 firmly down upon the bottom of the annular groove 35 in the tool 30.

The tool 30 is thus axially and circumferentially locked within the lock device 40 and sleeve 11. This places the apparatus 10 in condition for surgical use.

To remove the tool from the lock device 40 and sleeve 11, it suffices merely to fully push in the lock cup 77, from its FIG. 3C and 5 and 11 position to its FIG. 3B and 4 and 10 position. This brings the notch 101 of the lock plate 76 into occupancy by the release pin 84 and thereby allows the release spring 95 to drive the release pin 84 upward to fill the width of the notch 101 with the medium width part 88 of the release pin 84. Interference between the end of the notch 101 and the medium width portion 88 of the release pin 84 positively holds the lock plate 76 in its open (rightward-most in FIGS. 3B, 4 and 10) position. In this position of the lock plate 76, the hole 100 therein is coaxial with respect to the tool 30. Thus, as a result, the tool can simply be lifted out of the top of the sleeve 11 and the surrounding lock housing 52.

In this way, a succession of tools 30 can be inserted into the holder defined by the sleeve 11 and lock device 40 and held positively therein for appropriate surgical use.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. Surgical apparatus in which a spring actuated locking device is provided for axially releasably locating an inner surgical tool within an outer sleeve, comprising:
   a sleeve;
   a lock housing movable on said sleeve for receiving and locking a tool in said sleeve;
   a lock member laterally movably guided on said lock housing between open and closed positions, said lock member having means engageable with a tool for axially locking the tool in the sleeve;
   means resiliently biasing said lock member to said closed position;
   means for holding said lock member in said open position against said resilient bias to receive a tool and alternatively actuable for releasing said lock member to its closed position for locking said tool axially with respect to said lock housing.

2. The apparatus of claim 1 in which said lock member comprises a lock plate laterally slidably received in a diametral undercut groove in the top of said lock housing and a lock cup pendently fixed at one end of said lock plate and opening toward the peripheral wall of said lock housing.

3. The apparatus of claim 2 in which said means resiliently biasing said lock member comprises a lock spring compressed between said lock cup and lock housing peripheral wall.

4. Surgical apparatus in which a spring actuated locking device is provided for axially releasably locating an inner surgical tool within an outer sleeve, comprising:
   a sleeve;
   a lock housing movable on said sleeve for receiving and locking a tool in said sleeve;
   a lock member laterally movably guided on said lock housing between open and closed positions, said lock member having means engageable with a tool for axially locking the tool in the sleeve;
   means resiliently biasing said lock member to said closed position;
   means for holding said lock member in said open position against said resilient bias to receive a tool and alternatively actuable for releasing said lock member to its closed position for locking said tool axially with respect to said lock housing, said lock member comprising a lock plate laterally slidably guided on said lock housing, said lock housing having a through opening coaxial with said sleeve for receiving a tool therethrough, said lock plate having a hole alternatively alignable with, and offsetable with respect to, said through opening in said lock housing, said means engageable with said tool being an edge of said hole in said lock plate.

5. The apparatus of claim 4 in which said lock plate has a notch communicating with said hole therein, said means for holding said lock member comprising a release pin received in said lock housing for movement transversely to said lock plate and having a first part receivable in said notch for holding said lock plate in said open position.

6. The apparatus of claim 5 in which said notch has a narrowed extension in said lock plate, said release pin having a narrowed second part alternatively receivable in said narrowed extension to allow said lock plate to assume its closed position.

7. The apparatus of claim 6 including a release pin spring in said lock housing arranged for urging said release pin first part toward said lock plate for reception in said notch when said lock plate is moved to its open position to hold said lock plate in such open position.

8. The apparatus of claim 7 in which said release pin is stepped to define successive narrow, medium, and large widths respectively receivable in said notch extension, receivable in said notch and receivable in said hole, said large with preventing escape of said release pin from said lock housing when overlaid by said notch or notch extension of said lock plate, said first part and narrowed second part of said release pin defining respectively said medium and narrow widths.

9. The apparatus of claim 5 in which said release pin has a head engageable by a tool inserted in said lock housing to depress said release pin sufficiently to disengage said first part thereof from said notch and allow said lock plate to close and thereby lock the tool on said lock housing.

10. The apparatus of claim 9 including a taper housing spring coating between said taper housing and lock housing for biasing said lock housing axially toward said sleeve, said lock member being engageable with a tool to lock same in a position seated coaxially positively against said frustoconical mouth and hence coaxially within said sleeve.

11. Surgical apparatus in which a spring actuated locking device is provided for axially releasably locating an inner surgical tool within an outer sleeve, comprising:
a sleeve;
a lock housing movable on said sleeve for receiving and locking a tool in said sleeve;
a lock member laterally movably guided on said lock housing between open and closed positions, said lock member having means engageable with a tool for axially locking the tool in the sleeve;
means resiliently biasing said lock member to said closed position;
means for holding said lock member in said open position against said resilient bias to receive a tool and alternatively actuable for releasing said lock member to its closed position for locking said tool axially with respect to said lock housing, said sleeve including a taper housing with said lock housing and having and upward facing frustoconical mouth for receiving a tapered part of a tool, said lock housing being coaxial with and axially movable with respect to said taper housing.

12. Surgical apparatus in which a spring actuated locking device is provided for axially releasably locating an inner surgical tool within an outer sleeve, comprising:
a sleeve;
a lock housing movable on said sleeve for receiving and locking a tool in said sleeve;
a lock member laterally movably guided on said lock housing between open and closed positions, said lock member having means engageable with a tool for axially locking the tool in the sleeve;
means resiliently biasing said lock member to said closed position;
means for holding said lock member in said open position against said resilient bias to receive a tool and alternatively actuable for releasing said lock member to its closed position for locking said tool axially with respect to said lock housing,
eccentric means on said lock housing for engaging a tool to thereby fix the tool against rotation with respect to said lock member and thereby positively circumferentially orient the tool with respect to the lock member.

13. Surgical apparatus in which a locking device is provided for releasably securing a surgical tool in a sleeve, comprising:
a tool receiving sleeve;
a lock housing movable on said sleeve, said lock housing having a through opening through which the tool is insertable to be received into said sleeve;
a lock member on said lock housing and having a push button actuable for fixing said lock housing to an open position permitting reception of said tool through said through opening in said lock housing and into said sleeve, said lock member having means for automatically locking said tool against removal from said lock housing upon release of said push button;
taper means on said sleeve for receiving a correspondingly tapered portion of the tool to thereby assure a snug fitting connection of said sleeve with tool;
hand engageable means on said lock housing and actuable for pulling said lock housing axially with respect to said sleeve in a direction opposite the direction in which the tool is inserted into the sleeve and for engaging the lock member with a corresponding part of the tool and thereby for positively axially holding together the taper means of the sleeve and tapered portion of the tool while locking said tool axially with respect to said sleeve.

14. The apparatus of claim 13 including circumferential indexing means on said lock housing and engageable with the tool to locate the tool in a particular circumferential orientation with respect to the sleeve.

* * * * *

UNITED STATES PATENT AND TRADEMARK OFFICE
CERTIFICATE OF CORRECTION

PATENT NO. : 5,171,245
DATED : December 15, 1992
INVENTOR(S) : Haim CEZANA It is certified that error appears in the above-identified patent and that said Letters Patent is hereby corrected as shown below:

```
Column  9, line 18; replace "with" with ---width---.
           line 31; replace "coating" with ---coacting---.
           line 56; replace "with" with ---within---.
           line 57; replace "and" (second occurrence) with
                    ---an---.
Column 10, line 20; replace "housing," with ---housing;---.
```

Signed and Sealed this

Sixteenth Day of November, 1993

*Attest:*

BRUCE LEHMAN

*Attesting Officer*      *Commissioner of Patents and Trademarks*